United States Patent [19]

Nakao et al.

[11] Patent Number: 4,543,354
[45] Date of Patent: Sep. 24, 1985

[54] ANTI-HYPERTENSIVE 9-AMINOMETHYL-BENZO[f]QUINOLINE-3,10-DIONE DERIVATIVES

[75] Inventors: Toru Nakao; Tsuguo Ikebe; Tetsuya Tahara; Yutaka Maruyama, all of Oita; Osamu Yaoka, Fukuoka, all of Japan

[73] Assignee: Yoshitomi Pharmaceutical Industries, Ltd., Osaka, Japan

[21] Appl. No.: 550,423

[22] Filed: Nov. 10, 1983

[30] Foreign Application Priority Data

Nov. 10, 1982 [WO] PCT Int'l Appl. ... PCT/JP82/00438

[51] Int. Cl.⁴ ............... A61K 31/47; G07D 221/10
[52] U.S. Cl. ................... 514/238; 514/253; 514/290; 544/126; 544/361; 546/101
[58] Field of Search ............ 546/101; 544/126, 361; 424/258, 250, 248.56

[56] References Cited

U.S. PATENT DOCUMENTS 3,043,842  7/1962  Craig ................. 424/251 X
4,341,786  7/1982  DeMarinis et al. .......... 424/258

FOREIGN PATENT DOCUMENTS 0082371  5/1982  Japan ................. 546/101

OTHER PUBLICATIONS

Bardou, et al., Chemical Abstracts, vol. 67, 73,550x (1967).
Miana, et al., Chemical Abstracts, vol. 70, 77405p (1969).
Patel, et al., Chemical Abstracts, vol. 80, 14608t (1974).
Houben-Weil, Methoden der Organische Chemie, vol. XI/1, Stickstoff-verbindungen II, Amine, Georg Thieme Verlag, Stuttgart (1957), pp. 248–267.
McOmie, Protective Groups in Organic Chemistry, Plenum Press, New York (1973), pp. 62–63.

Primary Examiner—Donald G. Daus
Assistant Examiner—Diana G. Rivers
Attorney, Agent, or Firm—Sughrue, Mion, Zinn, Macpeak & Seas

[57] ABSTRACT

Benzo[f]quinoline derivatives which are useful as antihypertensive agents and are represented by the formula:

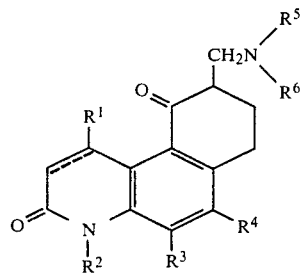

wherein $R^1$ is hydrogen or lower alkyl, $R^2$ is hydrogen, lower alkyl, hydroxy-lower-alkyl or lower-alkoxy-lower-alkyl, $R^3$ and $R^4$ are the same or different and each is hydrogen, lower alkyl, halogen, lower alkoxy, benzyloxy or hydroxy, $R^5$ and $R^6$ are the same or different and each is hydrogen, straight or branched alkyl, aralkyl or cycloalkyl, or $R^5$ and $R^6$ together with the adjacent nitrogen atom form a heterocycle, and the dotted line in the ring is an optional bond between 1- and 2-positions, and pharmaceutically acceptable acid addition salts thereof.

11 Claims, No Drawings

ANTI-HYPERTENSIVE 9-AMINOMETHYL-BENZO[f]QUINOLINE-3,10-DIONE DERIVATIVES

This invention relates to benzo[f]quinoline derivatives which are useful as medicines and are represented by the formula:

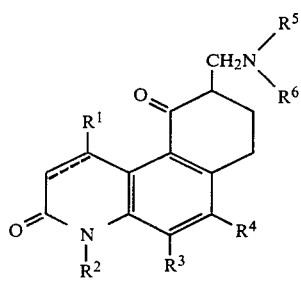
(I)

wherein $R^1$ is hydrogen or lower alkyl, $R^2$ is hydrogen, lower alkyl, hydroxy-lower-alkyl or lower-alkoxy-lower-alkyl, $R^3$ and $R^4$ are the same or different and each is hydrogen, lower alkyl, halogen, lower alkoxy, benzyloxy or hydroxy, $R^5$ and $R^6$ are the same or different and each is hydrogen, straight or branched alkyl, aralkyl or cycloalkyl, or $R^5$ and $R^6$ together with the adjacent nitrogen atom from a heterocycle, and the dotted line in the ring is an optional bond between 1- and 2-positions.

To be more precise in describing the above definitions, the lower alkyl means methyl, ethyl, propyl, isopropyl, butyl, etc., the hydroxy-lower-alkyl means hydroxyethyl, hydroxypropyl, etc., the lower-alkoxy-lower alkyl means methoxyethyl, ethoxyethyl, methoxypropyl, etc., the halogen means chlorine, bromine, fluorine, etc., the lower alkoxy means methoxy, ethoxy, propoxy, isopropoxy, butoxy, etc., the straight or branched alkyl means methyl, ethyl, propyl, isopropyl, butyl, isobutyl, amyl, isoamyl, hexyl, octyl, decyl, etc., the aralkyl means benzyl, phenethyl, phenylpropyl, phenylbutyl, etc. which may have substituents such as hydroxy, halogen, lower alkyl, lower alkoxy and sulfamoyl on the benzene ring, the cycloalkyl means cyclopentyl, cyclohexyl, etc., and the heterocycle formed by $R^5$ and $R^6$ together with the adjacent nitrogen atom means pyrrolidine, piperidine, morpholine, N'-methylpiperazine, 6,7-dimethoxy-1,2,3,4-tetrahydro-isoquinoline, etc.

The compounds of formula (I) can be produced by the following methods, for example.

METHOD 1

A method of subjecting to the so-called Mannich reaction a compound of the formula:

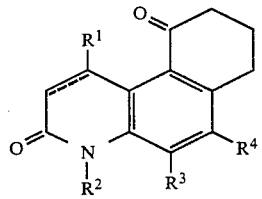
(II)

wherein each symbol is as defined above, with formaldehyde (used as formalin or paraformaldehyde) and a compound of the formula:

(III)

or an acid addition salt thereof, wherein each symbol is as defined above.

The reaction can be carried out under the well known conditions of Mannich reaction, but advantageously carried out in acetic anhydride or acetic acid at 50°–100° C. for 1–10 hours, or in an lower alkanol (ethanol, etc.) under reflux for 10–72 hours.

METHOD 2

A method of subjecting to reductive debenzylation a compound of the formula:

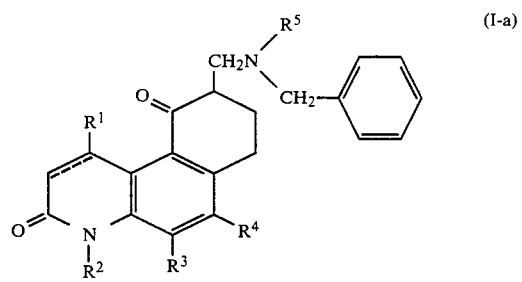
(I-a)

wherein each symbol is as defined above. In accordance with this method, the compounds of formula (I) wherein $R^6$ is hydrogen are obtained. It goes without saying that these compounds can also be produced by Method 1.

The conventional debenzylation is applied to this reaction, and, for example, the reaction suitably proceeds in ethanol in the presence of palladium-on-carbon catalyst under an atmosphere of hydrogen.

METHOD 3

A method of converting the amino group —$N(R^5)(R^6)$ into the amino group —$N(R^7)(R^8)$ by reacting a compound of formula (I) obtained by Method 1 or 2 or a compound which is obtained by the reaction of the compound of formula (I) with methyl iodide and have the formula:

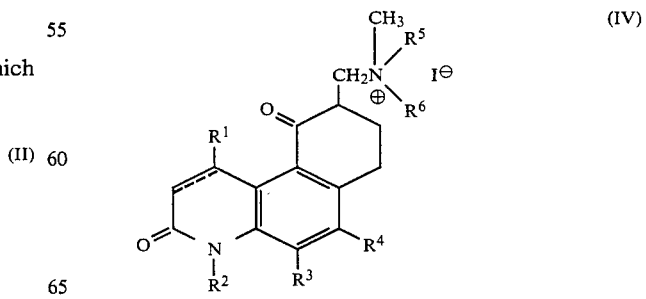
(IV)

wherein each symbol is as defined above, with a compound of the formula:

wherein $R^7$ and $R^8$ are as defined for $R^5$ and $R^6$, but $-N(R^7)(R^8)$ is different from $-N(R^5)(R^6)$.

The reaction suitably proceeds by refluxing in an lower alkanol by use of an excess amine (V).

METHOD 4

A method of reacting a compound, which is a compound of formula (I) wherein $R^2$ is hydrogen, of the formula:

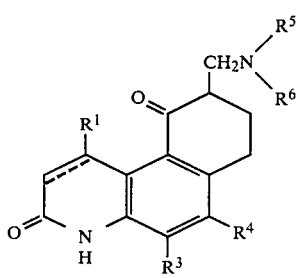

wherein each symbol is as defined above, with a compound of the formula:

$$R^9-X \qquad (VI)$$

wherein $R^9$ is lower alkyl, hydroxy-lower-alkyl or lower-alkoxy-lower-alkyl, and X is halogen such as chlorine or bromine. In accordance with this method, the compounds of formula (I) wherein $R^2$ is other than hydrogen are obtained. It goes without saying that these compounds can also be produced by Methods 1 to 3.

The reaction is usually carried out in an inert solvent such as N-methylpyrrolidone, N,N-dimethylformamide or N,N-dimethylacetamide, in the presence of an acid acceptor such as sodium amide, sodium ethylate, sodium hydride, potassium hydride or potassium amide. For instance, the reaction suitably proceeds in N,N-dimethylformamide in the presence of sodium hydride.

The starting compounds of formula (II) can be produced, for example, by subjecting to ring closure a carboxylic acid of the formula:

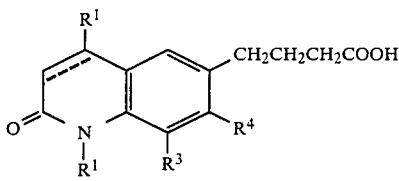

or a functional derivative thereof (e.g. acid halide), wherein each symbol is as defined above, in the presence of a Lewis acid such as sulfuric acid, polyphosphoric acid or aluminum chloride (cf. Japanese Patent Publication (unexamined) No. 57-82371).

The thus obtained compounds of formula (I) can be converted into the pharmaceutically acceptable acid addition salts by treating the compound with an inorganic acid such as hydrochloric acid, sulfuric acid, phosphoric acid or nitric acid or an organic acid such as maleic acid, fumaric acid, oxalic acid, lactic acid, citric acid or tartaric acid.

The compounds of the present invention show antihypertensive action, cardiotonic action, inhibitory action on platelet aggregation or the like, especially excellent antihypertensive activity in spontaneously hypertensive rats (SHR). Moreover, an increase of heart rate is mentioned as an undesirable side effect in many of antihypertensive agents, but the compounds of the invention have no influence on the heart rate, and so are useful as therapeutic agents for hypertension with less tachycardia.

The antihypertensive activity and influence on the heart rate of the compounds of the present invention are shown below.

METHODS

Male spontaneously hypertensive rats (SHR) (13–16 weeks old) having maximum blood pressure greater than 180 mmHg were used. Rats were divided into groups having about equal blood pressure level. The test compounds were suspended in 0.5% methyl cellulose solution and were orally administered. Five hours later, systolic blood pressure was measured again. Rats were put in restrainers and then warmed at 40° C. in a heating chamber. The blood pressure was measured by a tail cuff method (NARCO, PE-300). In addition tail arterial pulse wave was conducted to a tachometer, and the heart rate was measured. The antihypertensive activity is shown as decrease (mmHg) against the initial blood pressure (mean value of each group of six animals), and the heart rate is shown as the absolute value obtained by the measurement.

| Test Compound Example No. | Dose mg/kg, p.o. | Antihypertensive Activity in SHR (mmHg) | | Heart Rate (beat/min) | |
|---|---|---|---|---|---|
| | | Initial Value | Decrease after 5 hrs | Initial Value | Value after 5 hrs |
| 3 | 3 | 195 ± 5 | −50 ± 4 | 330 ± 7 | 305 ± 7 |
| | 10 | 189 ± 6 | −71 ± 7 | 338 ± 16 | 316 ± 12 |
| 4 | 1 | 204 ± 3 | −20 ± 7 | 314 ± 5 | 291 ± 7 |
| | 10 | 198 ± 9 | −102 ± 11 | 296 ± 10 | 300 ± 7 |
| 5 | 10 | 214 ± 6 | −49 ± 5 | 298 ± 6 | 320 ± 14 |
| 9 | 10 | 205 ± 6 | −36 ± 4 | 322 ± 19 | 300 ± 12 |
| 14 | 10 | 225 ± 7 | −36 ± 5 | 366 ± 17 | 309 ± 10 |
| 17 | 10 | 210 ± 6 | −60 ± 3 | 298 ± 10 | 305 ± 7 |
| 18 | 3 | 203 ± 10 | −42 ± 5 | 303 ± 7 | 288 ± 12 |
| | 10 | 219 ± 7 | −84 ± 7 | 331 ± 13 | 346 ± 15 |
| 20 | 10 | 229 ± 9 | −56 ± 7 | 304 ± 10 | 297 ± 8 |
| 21 | 10 | 223 ± 6 | −43 ± 6 | 314 ± 12 | 310 ± 5 |
| 28 | 10 | 222 ± 9 | −86 ± 6 | 355 ± 7 | 292 ± 8 |

-continued

| Test Compound | Dose | Antihypertensive Activity in SHR (mmHg) | | Heart Rate (beat/min) | |
|---|---|---|---|---|---|
| Example No. | mg/kg, p.o. | Initial Value | Decrease after 5 hrs | Initial Value | Value after 5 hrs |
| 31 | 10 | 217 ± 8 | −85 ± 8 | 349 ± 14 | 329 ± 15 |
| 32 | 10 | 239 ± 5 | −98 ± 7 | 358 ± 15 | 309 ± 4 |
| 33 | 10 | 248 ± 7 | −106 ± 8 | 346 ± 10 | 323 ± 5 |

The compounds of the present invention when used as antihypertensive agents can be administered orally or parenterally in the form of tablets, capsules, granules, powders, injectable solutions or the like admixed with a pharmaceutically acceptable and suitable carrier, vehicle, diluent or the like. The daily dose for human adults usually ranges from about 1 mg to about 50 mg for oral administration, but it may vary depending upon the age, body weight, and/or severity of the conditions to be treated as well as the response to the medication.

The present invention will be further illustrated in detail by the following examples, but they are not to be construed as limiting the present invention.

EXAMPLE 1

Diethylamine hydrochloride (8.3 g) is mixed with 6 ml of 37% formalin at room temperature for 30 minutes whereupon 40 ml of acetic anhydride is added dropwise at 60°–70° C. with stirring. After about 1 hour 11.5 g of 6-methyl-1,2,3,4,7,8,9,10-octahydro-benzo[f]quinoline-3,10-dione is added, and the resulting mixture is kept at 60°–70° C. for 3 hours. The reaction mixture is then concentrated under reduced pressure. To the residue is added 200 ml of acetone, and the mixture is heated under reflux for 10 minutes and then allowed to stand at room temperature. The precipitated crystals are collected by filtration and recrystallized from ethanol to give 7.0 g of 9-diethylaminomethyl-6-methyl-1,2,3,4,7,8,9,10-octahydro-benzo[f]quinoline-3,10-dione hydrochloride as colorless needles, melting at 196°–197° C.

EXAMPLE 2

N-Benzyl-N-butylamine hydrochloride (12 g), 6 ml of 37% formalin, 40 ml of acetic anhydride and 11.5 g of 6-methyl-1,2,3,4,7,8,9,10-octahydro-benzo[f]quinoline-3,10-dione are allowed to react and post-treated in the same manner of Example 1. The obtained crystals are recrystallized from isopropanol to give 13.2 g of 9-(N-benzyl-N-butylaminomethyl)-6-methyl-1,2,3,4,7,8,9,10-octahydro-benzo[f]quinoline-3,10-dione as colorless needles, melting at 190°–193° C.

EXAMPLE 3

9(N-Benzyl-N-butylaminomethyl)-6-methyl-1,2,3,4,7,8,9,10-octahydro-benzo[f]quinoline-3,10-dione hydrochloride (10 g) is dissolved in 300 ml of ethanol whereupon 2 g of 10% palladium-on-carbon is added, and the whole is kept under an atmosphere of hydrogen for 3 hours. The product partially crystallized out is dissolved well by adding methanol, and the catalyst is filtered off. The solvent is distilled off under reduced pressure, and the remaining crystals are recrystallized from ethanol to give 4.0 g of 9-butylaminomethyl-6-methyl-1,2,3,4,7,8,9,10-octahydro-benzo[f]quinoline-3,10-dione hydrochloride dihydrate as colorless needles, melting at 194°–196° C.

EXAMPLE 4

5-Chloro-1,2,3,4,7,8,9,10-octahydro-benzo[f]quinoline-3,10-dione (5.0 g), 3.3 g of butylamine hydrochloride and 2.7 g of paraformaldehyde are added to 100 ml of acetic acid, and the mixture is stirred at 50° C. for 4 hours. The acetic acid is distilled off under reduced pressure, 100 ml of acetone is added to the residue, and the resulting mixture is heated under reflux for 10 minutes. The precipitated crystals are collected by filtration to give 4.7 g of the crude product. The product is recrystallized from isopropanol to give 9-butylaminomethyl-5-chloro-1,2,3,4,8,9,10-octahydro-benzo[f]quinoline-3,10-dione hydrochloride as colorless needles, melting at 155°–157° C.

EXAMPLE 5

Phenethylamine hydrochloride (4.7 g), 2.7 g of paraformaldehyde and 4.6 g of 6-methyl-1,2,3,4,7,8,9,10-octahydro-benzo[f]quinoline-3,10-dione are added to 200 ml of ethanol, and the mixture is stirred under reflux for 2 days. The reaction mixture is then cooled, and the precipitated crystals are collected by filtration and recrystallized from 60% ethanol to give 2.0 g of 6-methyl-1,2,3,4,7,8,9,10-octahydro-9-phenethylaminomethyl-benzo[f]quinoline-3,10-dione hydrochloride as colorless needles, melting at 190°–192° C.

EXAMPLE 6

9-Butylaminomethyl-4,6-dimethyl-1,2,3,4,7,8,9,10-octahydro-benzo[f]-quinoline-3,10-dione hydrochloride (3.5 g) is converted into the base by the use of 10% sodium hydroxide solution and extracted with 100 ml of chloroform. The extract is dried over potassium carbonate, and the solvent is distilled off under reduced pressure. The residue is dissolved in 50 ml of acetone whereupon 5 ml of methyl iodode is added to form the quarternary ammonium salt, and the mixture is concentrated under reduced pressure. The pasty crude quarternary salt is dissolved in 50 ml of ethanol whereupon 5 ml of morpholine is added, and the mixture is heated under reflux on a water bath for 3 hours. The reaction mixture is concentrated under reduced pressure, and the residue is extracted with 100 ml of ethyl acetate. The extract is washed with water and dried over potassium carbonate, and 23% hydrochloric acid-isopropanol solution is added. The precipitated crystals are collected by filtration and recrystallized from ethanol to give 1.8 g of 4,6-dimethyl-9-morpholinomethyl-1,2,3,4,7,8,9,10-octahydro-benzo[f]quinoline-3,10-dione hydrochloride as pale yellow needles, melting at 176°–178° C.

In the same manner of the above examples, the following compounds of Examples 7 to 63 are produced, for example:

(7) 9-Dimethylaminomethyl-6-methyl-1,2,3,4,7,8,9,10-octahydro-benzo[f]quinoline-3,10-dione hydrochloride, m.p. 202° C.

(8) 6-Methyl-9-piperidinomethyl-1,2,3,4,7,8,9,10-octahydro-benzo[f]quinoline-3,10-dione hydrochloride, m.p 209°–210° C.

(9) 9-Dibutylaminomethyl-6-methyl-1,2,3,4,7,8,9,10-octahydro-benzo[f]quinoline-3,10-dione hydrochloride, m.p. 253°–255° C.

(10) 6-Methyl-9-octylaminomethyl-1,2,3,4,7,8,9,10-octahydro-benzo[f]quinoline-3,10-dione hydrochloride, m.p. 154°–157° C.

(11) 9-(N-Benzyl-N-octylaminoethyl)-6-methyl-1,2,3,4,7,8,9,10-octahydro-benzo[f]quinoline-3,10-dione hydrochloride, m.p. 149°–150° C.

(12) 9-Benzylaminomethyl-6-methyl-1,2,3,4,7,8,9,10-octahydro-benzo[f]quinoline-3,10-dione hydrochloride, m.p. 181°–183° C.

(13) 9-Dibenzylaminomethyl-6-methyl-1,2,3,4,7,8,9,10-octahydro-benzo[f]quinoline-3,10-dione hydrochloride, m.p. 218°–221° C.

(14) 9-Isopropylaminomethyl-6-methyl-1,2,3,4,7,8,9,10-octahydro-benzo[f]quinoline-3,10-dione hydrochloride hemihydrate, m.p. 209°–210° C.

(15) 9-(N-Benzyl-N-isopropylaminomethyl)-6-methyl-1,2,3,4,7,8,9,10-octahydro-benzo[f]quinoline-3,10-dione hydrochloride, m.p. 183°–184° C.

(16) 9-(N-Benzyl-N-hexylaminoethyl)-6-methyl-1,2,3,4,7,8,9,10-octahydro-benzo[f]quinoline-3,10-dione hydrochloride, m.p. 157°–159° C.

(17) 9-Hexylaminomethyl-6-methyl-1,2,3,4,7,8,9,10-octahydro-benzo[f]quinoline-3,10-dione hydrochloride monohydrate, m.p. 141°–143° C.

(18) 5-Chloro-9-phenethylaminomethyl-1,2,3,4,7,8,9,10-octahydro-benzo[f]quinoline-3,10-dione hydrochloride hemihydrate, m.p. 149°–151° C.

(19) 9-(6,7-Dimethoxy-1,2,3,4-tetrahydro-2-isoquinolyl)methyl)-6-methyl-1,2,3,4,7,8,9,10-octahydro-benzo[f]quinoline-3,10-dione hydrochloride, m.p. 216°–218° C.

(20) 9-Hexylaminomethyl-1,5-dimethyl-1,2,3,4,7,8,9,10-octahydro-benzo[f]quinoline-3,10-dione hydrochloride, m.p. 182°–184° C.

(21) 9-Butylaminomethyl-1,5-dimethyl-1,2,3,4,7,8,9,10-octahydro-benzo[f]quinoline-3,10-dione hydrochloride, m.p. 193°–195° C.

(22) 1,5-Dimethyl-9-methylaminomethyl-1,2,3,4,7,8,9,10-octahydro-benzo-[f]quinoline-3,10-dione hydrochloride, m.p. 214°–217° C.

(23) 5-Chloro-9-(3-phenylpropylaminomethyl)-1,2,3,4,7,8,9,10-octahydrobenzo[f]quinoline-3,10-dione hydrochloride, m.p. 138°–140° C.

(24) 5-Chloro-9-(p-hydroxyphenethylaminoethyl)-1,2,3,4,7,8,9,10-octahydro-benzo[f]quinoline-3,10-dione hydrochloride hemihydrate, m.p. 183°–186° C.

(25) 5-Chloro-9-(4-phenylbutylaminomethyl)-1,2,3,4,7,8,9,10-octahydrobenzo[f]quinoline-3,10-dione hydrochloride hemihydrate, m.p. 130°–133° C.

(26) 5-Chloro-9-(p-sulfamoylphenethylaminomethyl)-1,2,3,4,7,8,9,10-octahydro-benzo[f]quinoline-3,10-dione hydrochloride, m.p. 203°–205° C.

(27) 9-(N-Benzyl-N-butylaminomethyl)-1,5-dimethyl-1,2,3,4,7,8,9,10-octahydro-benzo[f]quinoline-3,10-dione hydrochloride, m.p. 145°–147° C.

(28) 9-Butylaminomethyl-4,6-dimethyl-1,2,3,4,7,8,9,10-octahydro-benzo[f]quinoline-3,10-dione hydrochloride, m.p. 190°–192° C.

(29) 9(N-benzyl-N-butylaminomethyl)-5-chloro-1,2,3,4,7,8,9,10-octahydrobenzo[f]quinoline-3,10-dione hydrochloride hemihydrate, m.p. 116°–118° C.

(30) 9-Butylaminomethyl-1,2,3,4,7,8,9,10-octahydro-benzo[f]quinoline-3,10-dione hydrochloride, m.p. 202°–204° C.

(31) 9-Amylaminomethyl-5-chloro-1,2,3,4,7,8,9,10-octahydro-benzo[f]quinoline-3,10-dione hydrochloride, m.p. 172°–174° C.

(32) 5-Bromo-9-butylaminomethyl-1,2,3,4,7,8,9,10-octahydro-benzo[f]quinoline-3,10-dione hydrochloride, m.p. 150°–153° C.

(33) 9-Butylaminomethyl-6-methoxyl-1-1,2,3,4,7,8,9,10-octahydrobenzo[f]quinoline-3,10-dione hydrochloride, m.p. 195°–198° C.

(34) 5-Chloro-9-dibutylaminomethyl-6-methyl-1,2,3,4,7,8,9,10-octahydrobenzo[f]quinoline-3,10-dione hydrochloride, m.p. 264°–266° C.

(35) 9-Ethylaminomethyl-6-methyl-1,2,3,4,7,8,9,10-octahydro-benzo[f]quinoline-3,10-dione hydrochloride, m.p. 218°–219° C.

(36) 9-Butylaminomethyl-4-methyl-1,2,3,4,7,8,9,10-octahydro-benzo[f]quinoline-3,10-dione hydrochloride hemihydrate, m.p. 175°–178° C.

(37) 9-Dibutylaminomethyl-4-(2-ethoxyethyl)-1,2,3,4,7,8,9,10-octahydrobenzo[f]quinoline-3,10-dione hydrochloride, m.p. 147°–149° C.

(38) 6Methyl-9-morpholinomethyl-3,4,7,8,9,10-hexahydro-benzo[f]quinoline-3,10-dione hydrochloride hemihydrate, m.p. 192°–195° C.

(39) 9-Dibutylaminomethyl-6-methyl-3,4,7,8,9,10-hexahydro-benzo[f]quinoline-3,10-dione hydrochloride hemihydrate, m.p. 250° C.

(40) 9-Butylaminomethyl-6-methyl-3,4,7,8,9,10-hexahydro-benzo[f]quinoline-3,10-dione hydrochloride hemihydrate, m.p. 196°–197° C.

(41) 9-(N-Benzyl-N-butylaminomethyl)-6-methoxy-4-methyl-1,2,3,4,7,8,9,10-octahydro-benzo[f]quinoline-3,10-dione

(42) 9-Butylaminomethyl-6-methoxy-4-methyl-1,2,3,4,7,8,9,10-octahydrobenzo[f]quinoline-3,10-dione

(43) 9-Butylaminomethyl-4-(2-ethoxyethyl)-6-methyl-1,2,3,4,7,8,9,10-octahydro-benzo[f]quinoline-3,10-dione

(44) 9-Dibutylaminomethyl-4(2-ethoxyethyl)-6-methyl-1,2,3,4,7,8,9,10-octahydro-benzo[f]quinoline-3,10-dione

(45) 9-Butylaminomethyl-1,5-dimethyl-3,4,7,8,9,10-hexahydro-benzo[f]quinoline-3,10-dione

(46) 1,5-Dimethyl-9-morpholinomethyl-3,4,7,8,9,10-hexahydro-benzo[f]quinoline-3,10-dione

(47) 9-Butylaminomethyl-5-chloro-6-methyl-1,2,3,4,7,8,9,10-octahydrobenzo[f]quinoline-3,10-dione

(48) 5Chloro-6-methyl-9-morpholinomethyl-1,2,3,4,7,8,9,10-octahydrobenzo[f]quinoline-3,10-dione

(49) 6-Benzyloxy-9-butylaminomethyl-1-methyl-1,2,3,4,7,8,9,10-octahydrobenzo[f]quinoline-3,10-dione

(50) 6-Benzyloxy-1-methyl-9-morpholinomethyl-1,2,3,4,7,8,9,10-octahydrobenzo[f]quinoline-3,10-dione

(51) 9-Butylaminomethyl-6-hydroxyl-1-methyl-1,2,3,4,7,8,9,10-octahydrobenzo[f]quinoline-3,10-dione

(52) 6-Hydroxy-1-methyl-9-morpholinomethyl-1,2,3,4,7,8,9,10-octahydrobenzo[f]quinoline-3,10-dione

(53) 6-Methoxy-1-methyl-9-morpholinomethyl-1,2,3,4,7,8,9,10-octahydrobenzo[f]quinoline-3,10-dione
(54) 1,5Dimethyl-9-(4-methyl-1-piperazinylmethyl)-3,4,7,8,9,10-hexahydrobenzo[f]quinoline-3,10-dione
(55) 5-Bromo-9-cyclohexylaminomethyl-1,2,3,4,7,8,9,10-octahydro-benzo[f]quinoline-3,10-dione
(56) 5-Methoxy-9-phenethylaminomethyl-1,2,3,4,7,8,9,10-octahydro-benzo[f]quinoline-3,10-dione
(57) 5-Hydroxy-9-phenethylaminomethyl-1,2,3,4,7,8,9,10-octahydro-benzo[f]quinoline-3,10-dione
(58) 9-Butylaminomethyl-5-methoxy-1,2,3,4,7,8,9,10-octahydro-benzo[f]quinoline-3,10-dione
(59) 9-Butylaminomethyl-5-chloro-4-methyl-1,2,3,4,7,8,9,10-octahydrobenzo[f]quinoline-3,10-dione
(60) 9-Butylaminomethyl-5-chloro-4-(2-hydroxyethyl)-1,2,3,4,7,8,9,10-octahydro-benzo[f]quinoline-3,10-dione
(61) 5-Chloro-4-(2-methoxyethyl)-9-phenethylaminomethyl-1,2,3,4,7,8,9,10-octahydro-benzo[f]quinoline-3,10-dione
(62) 9-Butylaminomethyl-4-(2-hydroxyethyl)-6-methyl-1,2,3,4,7,8,9,10,-octahydro-benzo[f]quinoline-3,10-dione
(63) 4-Butyl-9-butylaminomethyl-1,5-dimethyl-1,2,3,4,7,8,9,10-octahydrobenzo[f]quinoline-3,10-dione
(64) 4-(2-Hydroxyethyl)-1,5-dimethyl-9-morpholinomethyl-1,2,3,4,7,8,9,10-octahydro-benzo[f]quinoline-3,10-dione
(65) 9-(p-Chlorophenethylaminomethyl)-6-methyl-1,2,3,4,7,8,9,10-octahydrobenzo[f]quinoline-3,10-dione
(66) 5-Chloro-9-(p-methylphenethylaminomethyl)-1,2,3,4,7,8,9,10-octahydrobenzo[f]quinoline-3,10-dione
(67) 9-Cyclohexylaminomethyl-1,5-dimethyl-1,2,3,4,7,8,9,10-octahydrobenzo[f]quinoline-3,10-dione While the invention has been described in detail and with reference to specific embodiments thereof, it is apparent that various alterations and modifications can be made without departing from the spirit and scope thereof.

What is claimed is:

1. A benzo[f]quinoline derivative of the formula:

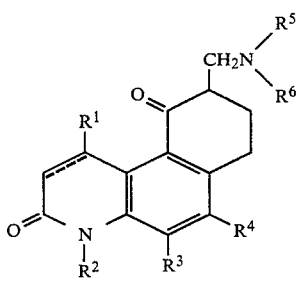

wherein $R^1$ is hydrogen or lower alkyl, $R^2$ is hydrogen, lower alkyl, hydroxy-lower-alkyl or lower-alkoxy-lower-alkyl, $R^3$ and $R^4$ are the same or different and each is hydrogen, lower alkyl, halogen, lower alkoxy, benzyloxy or hydroxy, $R^5$ and $R^6$ are the same or different and each is hydrogen, straight or branched $C_{1-10}$ alkyl, pheny-$C_{1-4}$ alkyl or $C_{5-6}$ cycloalkyl, or $R^5$ and $R^6$ together with the adjacent nitrogen atom form a pyrrolidine, piperidine, morpholine, N'-methylpiperazine, or 6,7-dimethyl-1,2,3,4,-tetrahydroisoquinoline, and the dotted line in the ring is an optional bond between the 1- and 2-positions, or a pharmaceutically acceptable acid addition salt thereof.

2. A benzo[f]quinoline derivative of the formula:

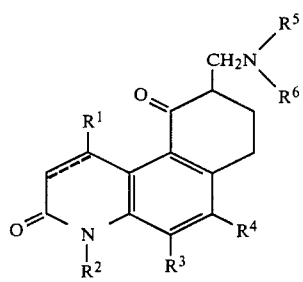

wherein $R^1$, $R^2$, $R^3$, $R^4$, $R^5$ and $R^6$ are as defined in claim 1, or a pharmaceutically acceptable acid addition salt thereof.

3. A benzo[f]quinoline derivative of the formula:

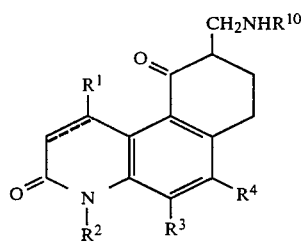

wherein $R^1$, $R^2$, $R^3$ and $R^4$ are as defined in claim 1, and $R^{10}$ is straight or branched alkyl, aralkyl or cycloalkyl, or a pharmaceutically acceptable acid addition salt thereof.

4. A compound of claim 1: 9-butylaminomethyl-6-methyl-1,2,3,4,7,8,9,10-octahydrobenzo[f]quinoline-3,10-dione.

5. A compound of claim 1: 9-butylaminomethyl-5-chloro-1,2,3,4,7,8,9,10-octahydrobenzo[f]quinoline-3,10-dione.

6. A compound of claim 1: 5-bromo-9-butylaminomethyl-1,2,3,4,7,8,9,10-octahydrobenzo[f]quinoline-3,10-dione.

7. A compound of claim 1: 9-butylaminomethyl-6-methoxy-1-methyl-1,2,3,4,7,8,9,10-octahydrobenzo[f]quinoline-3,10-dione.

8. A compound of claim 1: 9-butylaminomethyl-4,6-dimethyl-1,2,3,4,7,8,9,10-octahydrobenzo[f]quinoline-3,10-dione.

9. A compound of claim 1: 5-chloro-9-phenethylamonomethyl-1,2,3,4,7,8,9,10-octahydrobenzo[f]quinoline-3,10-dione.

10. A compound of claim 1: 9-hexylaminomethyl-6-methyl-1,2,3,4,7,8,9,10-octahydrobenzoe[f]quinoline-3,10-dione.

11. An antihypertensive composition comprising a compound of claim 1 in combination with a pharmaceutically acceptable inert carrier, said compound being present in a therapeutically effective amount.

* * * * *